(12) United States Patent
Tanigawa

(10) Patent No.: US 12,178,657 B2
(45) Date of Patent: Dec. 31, 2024

(54) ULTRASONIC IMAGE DISPLAY SYSTEM AND PROGRAM FOR COLOR DOPPLER IMAGING

(71) Applicant: GE Precision Healthcare LLC, Wauwatosa, WI (US)

(72) Inventor: Shunichiro Tanigawa, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/570,207

(22) Filed: Jan. 6, 2022

(65) Prior Publication Data

US 2022/0211353 A1    Jul. 7, 2022

(30) Foreign Application Priority Data

Jan. 6, 2021    (JP) ................................. 2021-000856

(51) Int. Cl.
*A61B 8/08* (2006.01)
*A61B 8/06* (2006.01)

(52) U.S. Cl.
CPC .............. *A61B 8/5246* (2013.01); *A61B 8/06* (2013.01); *A61B 8/488* (2013.01); *A61B 8/5207* (2013.01)

(58) Field of Classification Search
CPC ......... A61B 8/5246; A61B 8/06; A61B 8/488; A61B 8/5207; A61B 8/0825; A61B 8/5223; A61B 8/4444; A61B 8/461; A61B 8/469; G06F 18/214; G06N 20/00

See application file for complete search history.

(56) References Cited

U.S. PATENT DOCUMENTS

| | | | |
|---|---|---|---|
| 9,913,575 B2* | 3/2018 | Gazdzinski | A61B 5/6861 |
| 10,945,678 B2* | 3/2021 | Oka | A61B 8/0825 |
| 2020/0345324 A1* | 11/2020 | Matsumoto | A61B 8/54 |
| 2020/0359989 A1* | 11/2020 | Miyachi | A61B 8/488 |
| 2022/0096053 A1* | 3/2022 | Sethuraman | A61B 8/4488 |
| 2022/0148158 A1* | 5/2022 | Ayinde | A61B 8/08 |

FOREIGN PATENT DOCUMENTS

| | | | |
|---|---|---|---|
| JP | 2018153561 A | | 10/2018 |
| JP | 2019076541 A | | 5/2019 |
| JP | 2020092739 | * | 6/2020 |
| JP | 2020092739 A | | 6/2020 |
| KR | 20100025102 | * | 3/2010 |

* cited by examiner

*Primary Examiner* — Alexei Bykhovski

(57) ABSTRACT

To set parameters according to a body part of interest serving as a target for producing a color Doppler image, a processor in an ultrasonic image display system identifies a body part of interest serving as a target for producing a color Doppler image of a patient based on data for a B-mode image, and determines parameters regarding acquisition of data for the color Doppler image according to the body part of interest. The processor then controls an ultrasonic probe to perform a color Doppler scan for a color Doppler image on the patient using the determined parameters, and creates data for a color Doppler image based on echo data obtained by the color Doppler scan.

7 Claims, 11 Drawing Sheets

ULTRASONIC IMAGE DISPLAY SYSTEM AND PROGRAM FOR COLOR DOPPLER IMAGING

FIELD

The present invention relates to an ultrasonic image display system for determining parameters regarding acquisition of data for a color Doppler image according to a body part of interest, and a program for controlling the same.

BACKGROUND

In examinations using an ultrasonic diagnostic apparatus, which is an example of an ultrasonic image display system, a color Doppler image for observing blood flow or the like in a patient is produced and displayed based on ultrasonic echo signals to perform a diagnosis.

To produce a color Doppler image exhibiting correct blood flow in a color Doppler mode, an operator sets appropriate parameters according to a target to be observed in a patient, or selects a parameter set consisting of a group of appropriate parameters prepared beforehand according to an organ or the like desired to be examined. While it is desirable to thus set appropriate parameters according to a body part of interest serving as a target for producing a color Doppler image, such setting is often not satisfactorily performed because it is cumbersome for some users or the like to perform adjustment of appropriate parameters or selection of an appropriate model. Moreover, it is often difficult to produce a color Doppler image with appropriate parameters according to the body part of interest.

BRIEF SUMMARY

This summary introduces concepts that are described in more detail in the detailed description. It should not be used to identify essential features of the claimed subject matter, nor to limit the scope of the claimed subject matter.

An ultrasonic image display system, in one mode, comprises a processor and an ultrasonic probe. The processor is adapted to perform control comprising the acts of: controlling said ultrasonic probe to perform a B-mode scan for a B-mode image on a patient, and creating data for a B-mode image based on echo data obtained by the B-mode scan. The processor is also adapted to perform control comprising the acts of: identifying a body part of interest serving as a target for producing a color Doppler image of the patient based on the data for the B-mode image, and determining parameters regarding acquisition of data for the color Doppler image according to the body part of interest. The processor is further adapted to perform control comprising the acts of: controlling the ultrasonic probe to perform a color Doppler scan for a color Doppler image on the patient, and creating data for a color Doppler image based on echo data obtained by the color Doppler scan. At least one of the color Doppler scan and color Doppler image data creation is performed using the determined parameters.

An ultrasonic image display system, in another mode, is the ultrasonic image display system in the mode above, wherein said processor is adapted to identify a body part of the patient in a first region in the patient based on the data for the B-mode image in the first region, and identify the body part of interest based on the data for the B-mode image in a second region included in the first region. The body part of interest is included in the body part of the patient in the first region, and the second region is a target for producing a color Doppler image of the patient.

An ultrasonic image display system, in still another mode, is an ultrasonic image display system comprising a processor and an ultrasonic probe. The processor controls the ultrasonic probe to perform a B-mode scan for a B-mode image on a patient, and creates data for a B-mode image based on echo data obtained by the B-mode scan. The processor also defines a region of interest in the B-mode image, controls the ultrasonic probe to perform a first color Doppler scan for a first color Doppler image on the patient, and creates data for a first color Doppler image in the region of interest based on echo data obtained by the first color Doppler scan. The processor identifies a body part of the patient in a first region in the patient based on the data for the B-mode image in the first region. The first region includes said region of interest. The processor also identifies a body part of interest serving as a target in said region of interest in said patient based on the data for said first color Doppler image in a second region constituted by the region of interest. The body part of interest is included in the body part of said patient in the first region. The processor further determines parameters regarding acquisition of the data for a second color Doppler image of the patient according to the body part of interest, controls the ultrasonic probe to perform a second color Doppler scan for a second color Doppler image on the patient, and creates data for the second color Doppler image based on echo data obtained by the second color Doppler scan. At least one of the color Doppler scan and second color Doppler image data creation is performed using the determined parameters.

According to the ultrasonic image display system in the one mode above, a body part of interest serving as a target for producing a color Doppler image is identified based on data for a B-mode image, and parameters regarding acquisition of the color Doppler image are determined according to the body part of interest. Therefore, parameters according to the body part of interest can be set by merely producing a B-mode image.

According to the ultrasonic image display system in the other mode above, after a body part of the patient including the body part of interest has been first identified, the body part of interest is identified from within the body part, and therefore, the body part of interest can be more correctly identified.

Moreover, according to the ultrasonic image display system in the still another mode above, a body part of the patient in a first region including the body part of interest is first identified based on data for a B-mode image, and thereafter, the body part of interest is identified from within the body part based on data for a first color Doppler image. Therefore, the body part of interest can be more correctly identified. Parameters regarding acquisition of data for a second color Doppler image are then determined according to the body part of interest. Therefore, parameters according to the body part of interest can be set by merely producing a B-mode image and a first color Doppler image.

DETAILED DESCRIPTION

Now embodiments of the present invention will be described hereinbelow with reference to the accompanying drawings.

Figure 1:
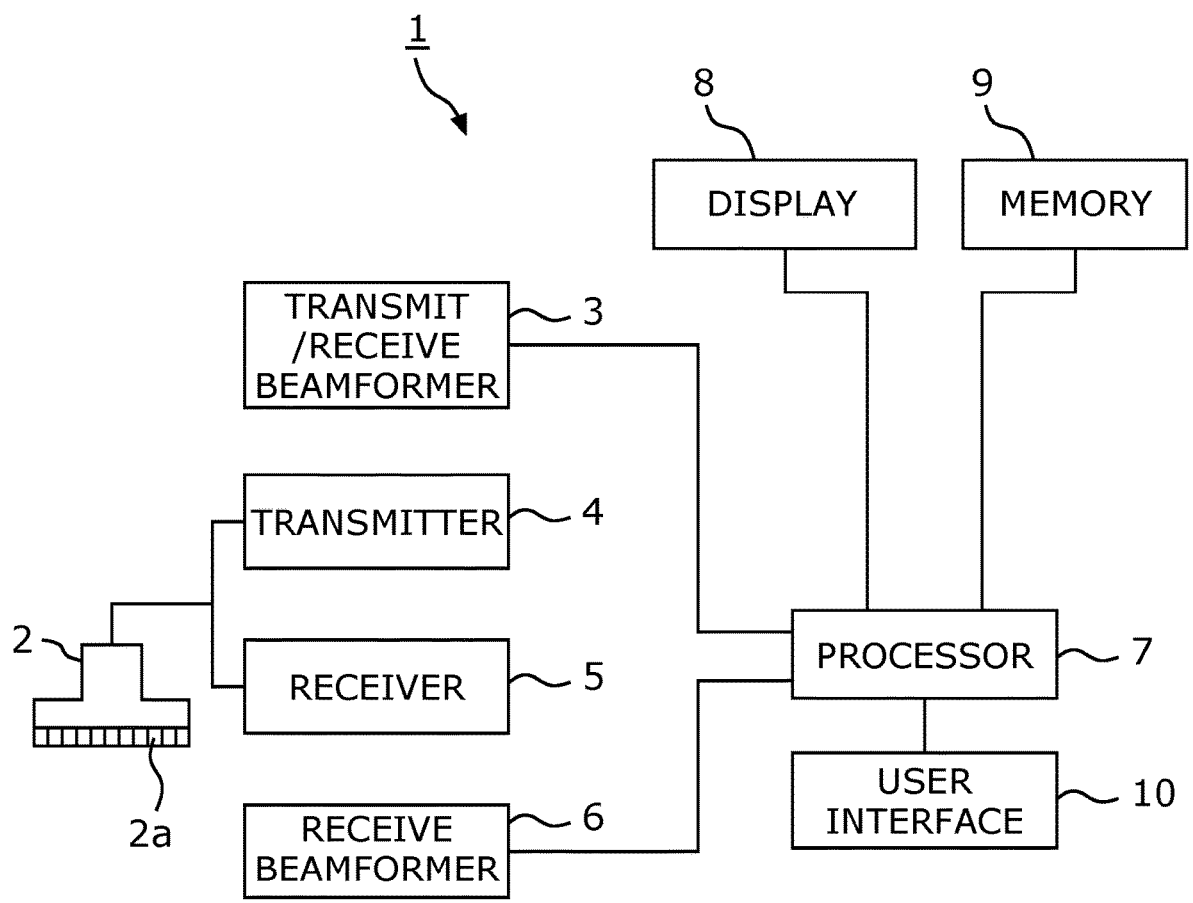
FIG. 1 is a block diagram showing an example of an ultrasonic image display system in accordance with an embodiment.

To begin with, a first embodiment will be described. An ultrasonic image display system 1 shown in FIG. 1 is an ultrasonic diagnostic apparatus in an example, and comprises an ultrasonic probe 2, a transmit beamformer 3, and a transmitter 4. The ultrasonic probe 2 performs an ultrasonic scan on a patient, and receives ultrasonic echoes. The ultrasonic scan includes a B-mode scan and a color Doppler scan, which will be discussed later.

More specifically, the ultrasonic probe 2 has a plurality of vibration elements 2a for emitting pulsed ultrasound to the patient (not shown). The plurality of vibration elements 2a are driven by the transmit beamformer 3 and transmitter 4 to emit pulsed ultrasound.

The ultrasonic image display system 1 further comprises a receiver 5 and a receive beamformer 6. The pulsed ultrasound emitted from the vibration elements 2a is reflected in the inside of the patient to generate echoes returning to the vibration elements 2a. The echoes are converted into electrical signals by the vibration elements 2a, which are echo signals, and are input to the receiver 5. The echo signals undergo amplification, etc. with a required gain at the receiver 5, and then input to the receive beamformer 6, where receive beamforming is performed. The receive beamformer 6 outputs receive-beamformed ultrasound data.

The receive beamformer 6 may be a hardware beamformer or a software beamformer. In the case that the receive beamformer 6 is a software beamformer, it may comprise one or more processors including one or more of a graphics processing unit (GPU), a microprocessor, a central processing unit (CPU), a digital signal processor (DSP), or other kinds of processors capable of executing logical operations. The processor(s) constituting the receive beamformer 6 may be constructed from a processor separate from a processor 7 described later, or constructed from the processor 7.

The ultrasonic probe 2 may comprise electrical circuitry to perform all or part of transmit and/or receive beamforming. For example, all or part of the transmit beamformer 3, transmitter 4, receiver 5, and receive beamformer 6 may be situated within the ultrasonic probe 2.

The ultrasonic image display system 1 also comprises the processor 7 for controlling the transmit beamformer 3, transmitter 4, receiver 5, and receive beamformer 6. Moreover, the ultrasonic image display system 1 comprises a display 8, memory 9, and a user interface 10.

The processor 7 comprises one or more processors. The processor 7 is in electronic communication with the ultrasonic probe 2. The processor 7 may control the ultrasonic probe 2 to acquire ultrasound data. The processor 7 controls which of the vibration elements 2a are active, and the shape of an ultrasonic beam transmitted from the ultrasonic probe 2. The processor 7 is also in electronic communication with the display 8, and the processor 7 may process the ultrasound data into ultrasonic images for display on the display 8. The phrase "electronic communication" may be defined to include both wired and wireless connections. The processor 7 may include a central processing unit (CPU) according to one embodiment. According to other embodiments, the processor 7 may include other electronic components capable of carrying out processing functions, such as a digital signal processor, a field-programmable gate array (FPGA), a graphics processing unit (GPU), or any other type of processor. According to other embodiments, the processor 7 may include a plurality of electronic components capable of carrying out processing functions. For example, the processor 7 may include two or more electronic components selected from a list of electronic components including: a central processing unit, a digital signal processor, a field-programmable gate array, and a graphics processing unit.

The processor 7 may also include a complex demodulator (not shown) that demodulates RF data. In another embodiment, the demodulation can be carried out earlier in the processing chain.

The processor 7 is adapted to perform one or more processing operations according to a plurality of selectable ultrasonic modalities on the data. The data may be processed in real-time during a scanning session as the echo signals are received. For the purpose of this disclosure, the term "real-time" is defined to include a procedure that is performed without any intentional delay.

The data may be temporarily stored in a buffer (not shown) during ultrasonic scanning, so that they can be processed in a live operation or in an off-line operation not in real-time. In this disclosure, the term "data" may be used in the present disclosure to refer to one or more datasets acquired using an ultrasonic image display system.

The ultrasound data may be processed by the processor 7 in other or different mode-related modules (e.g., B-mode, color Doppler, M-mode, color M-mode, spectral Doppler, contrast-enhanced mode, elastography, TVI, strain, strain rate, and the like) to form data for ultrasonic images. For example, one or more modules may produce ultrasonic images in B-mode, color Doppler, M-mode, color M-mode, spectral Doppler, contrast-enhanced mode, elastography, TVI, strain, strain rate, and combinations thereof, and the like.

The image beams and/or image frames are stored and timing information indicating a time at which the data was acquired in memory may be recorded. The modules may include, for example, a scan conversion module to perform scan conversion operations to convert the image frames from coordinate beam space to display space coordinates. A video processor module may be provided that reads the image frames from memory and displays the image frames in real-time while a procedure is being carried out on the patient. The video processor module may store the image frames in image memory, from which the ultrasonic images are read and displayed on the display 8.

As used herein, the term "image" may broadly refer to both a visible image, and data representing a visible image. The term "data" may include both raw data that is ultrasound data before the scan conversion operations, and image data that is data after the scan conversion operations.

In the case that the processor 7 includes a plurality of processors, the aforementioned processing tasks to be handled by the processor 7 may be handled by the plurality of processors. For example, a first processor may be utilized to demodulate and decimate the RF signal while a second processor may be used to further process the data prior to displaying an image.

In the case that the receive beamformer 6 is a software beamformer, for example, its processing functions may be carried out by a single processor or by a plurality of processors.

The display 8 is an LED (Light Emitting Diode) display, an LCD (Liquid Crystal Display), an organic EL (Electro-Luminescence) display, or the like.

The memory 9 is any known data storage medium. In an example, the ultrasonic image display system 1 comprises non-transitory storage media and transitory storage media as the memory 9, and comprises a plurality of units of memory 9. The non-transitory storage medium is, for example, a non-volatile storage medium such as an HDD (Hard Disk Drive) and ROM (Read Only Memory). The non-transitory storage media may include a portable storage medium such as a CD (Compact Disc) and a DVD (Digital Versatile Disc). In the non-transitory storage medium, programs executed by the processor 7 are stored.

The transitory storage medium is a volatile storage medium such as RAM (Random Access Memory).

The user interface 10 can accept an operator's input. For example, the user interface 10 accepts an input of a command and/or information from the operator. The user interface 10 is constructed to include a keyboard, hard keys, a trackball, a rotary control, soft keys, and the like. The user interface 10 may include a touch screen that displays soft keys, etc.

Figure 2:
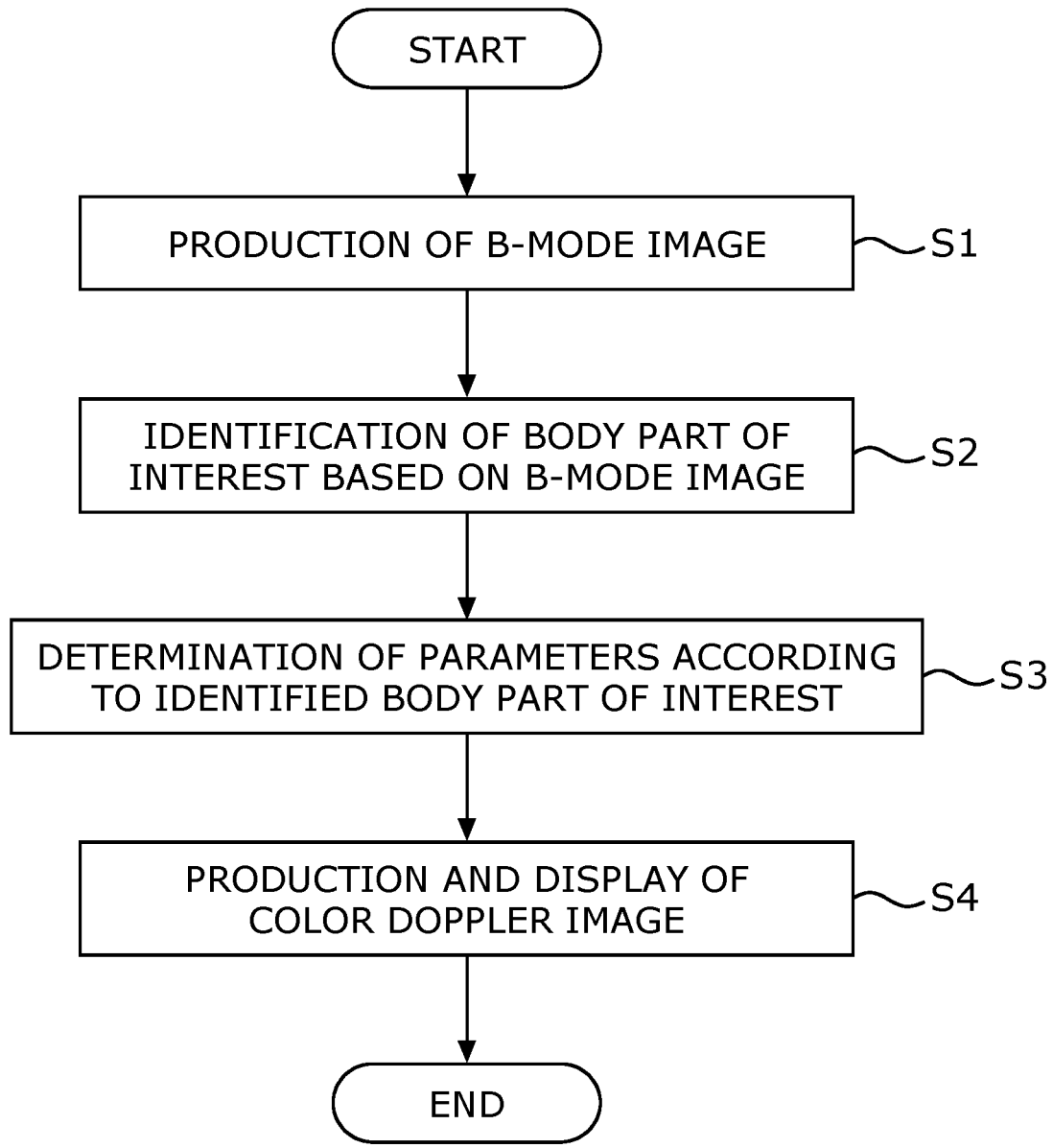
FIG. 2 is a flow chart showing an example of processing in the ultrasonic image display system in accordance with a first embodiment.

Next, an operation in the ultrasonic image display system 1 in the present embodiment will be described. Referring to the flow chart in FIG. 2, at Step S1, the processor 7 controls the ultrasonic probe 2 to perform a B-mode scan for a B-mode image on a patient. The processor 7 also creates data for a B-mode image based on echo data obtained by the B-mode scan.

Figure 3:
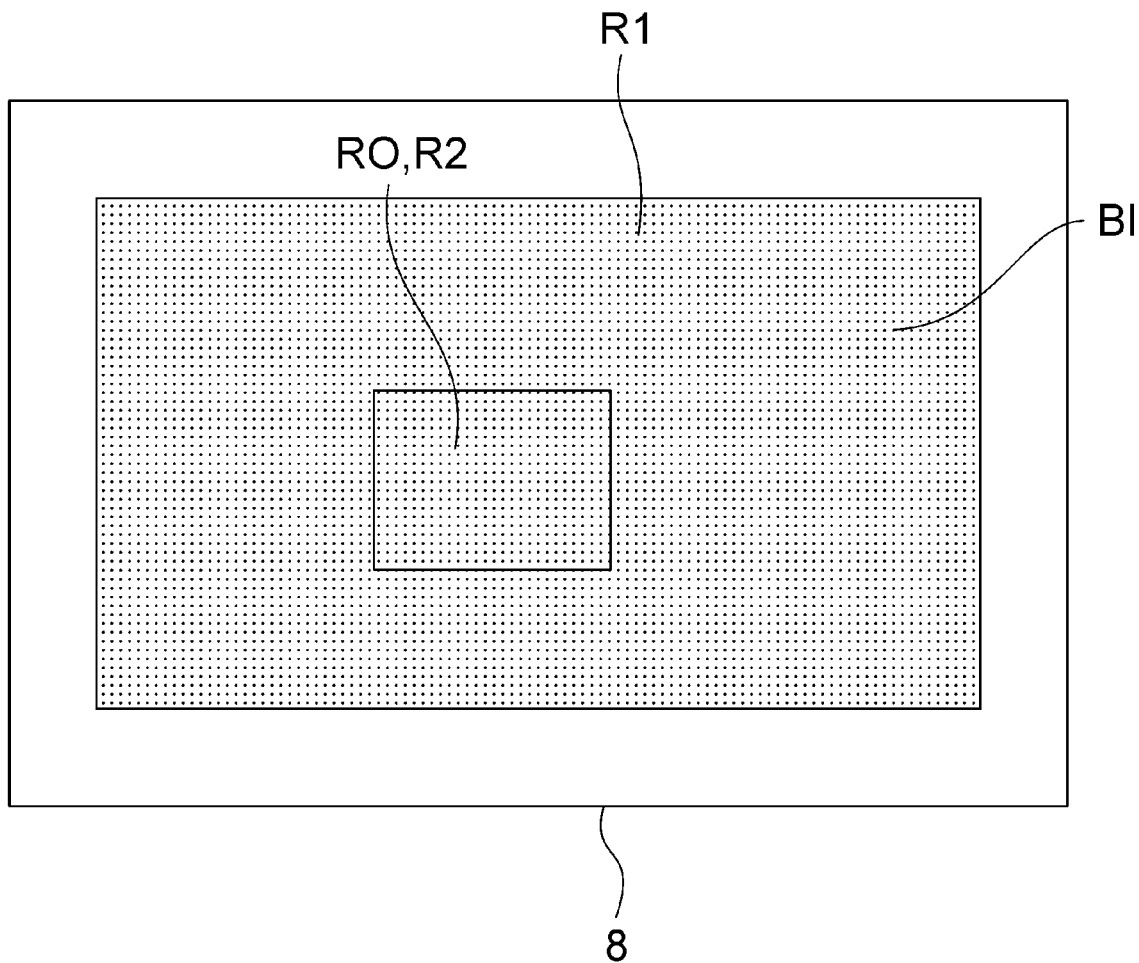
FIG. 3 is a diagram showing a display on which a B-mode image having a body part of interest defined therein is displayed.

At Step S1, the processor 7 may display a B-mode image BI on the display 8 based on the data for the B-mode image, as shown in FIG. 3. Moreover, the processor 7 may define a region of interest RO serving as a target for producing and displaying a color Doppler image in the B-mode image BI displayed on the display 8. In an example, once the user interface 10 has accepted an operator's input for defining a region of interest RO, the processor 7 defines the region of interest RO.

Next, at Step S2, the processor 7 identifies, based on the data for the B-mode image BI, a body part of interest serving as a target for producing a color Doppler image of the patient. The body part of interest is a body part of the patient in a region that corresponds to the region of interest RO. The processor 7 identifies as the body part of interest a body part of the patient for which the data for the B-mode image BI was acquired. The processor 7 may identify the body part of interest based on the data for the B-mode image BI in a first region greater than the region of interest RO. The first region is the whole or part of the acquired B-mode image BI. The first region includes the region of interest RO. In FIG. 3, Reference Symbol R1 designates the first region that is the whole of the B-mode image BI.

The processor 7 may also identify the body part of interest based on the data for the B-mode image BI in a second region R2 constituted by the region of interest RO.

The body part of interest includes a mammary gland, a neck, lower limbs, etc., in an example. The body part of interest further includes a thyroid gland and a carotid artery included in the neck, lower-limb veins and lower-limb arteries included in the lower limbs, etc. It will be easily recognized that the examples given here are merely illustrative.

The processor 7 may perform identification of the body part of interest using a learned model obtained by machine learning. This will now be particularly described. The memory 9 stores therein a learned model trained for a correlation between a B-mode image and an evaluation value for the B-mode image. The evaluation value is related to the body part of the patient serving as a candidate for the body part of interest. In an example, the evaluation value is the probability that the B-mode image matches an image of a body part of the patient. The learned model has an evaluation value learned for each of a plurality of body parts of the patient. The body parts of the patient may include the aforementioned mammary gland, neck, lower limbs, thyroid gland, carotid artery, lower-limb veins, and lower-limb arteries, in an example. The learned model here is assumed to have a correlation learned between a B-mode image, and each of the probabilities that the B-mode image is of the mammary gland, that it is of the thyroid gland, that it is of the carotid artery, that it is of the lower-limb veins, and that it is of the lower-limb arteries.

It should be noted that for the thyroid gland and carotid artery, B-mode images used in learning and those input to the learned model, which will be described later, are short-axis views, in an example. For the lower-limb veins and lower-limb arteries, B-mode images used in learning and those input to the learned model, which will be described later, are long-axis views, in an example.

The processor 7 inputs the data for the B-mode image BI acquired at Step S1 to an input layer of the learned model. The input data for the B-mode image BI is data in the first region R1 or that in the second region R2 (region of interest R). The processor 7 obtains, as an output of an output layer of the learned model, an evaluation value for the body part of the patient for the B-mode image BI input to the input layer. The evaluation value is, in an example, the probability that the B-mode image BI of the data input to the learned model matches an image of each of the body parts of the patient serving as a candidate for the body part of interest. Specifically, the evaluation values are the probabilities that the B-mode image BI of the data input to the learned model is of the mammary gland, that it is of the thyroid gland, that it is of the carotid artery, that it is of the lower-limb veins, and that it is of the lower-limb arteries.

The processor 7 identifies the body part of interest based on the evaluation value. The processor 7 identifies a body part with the highest evaluation value i.e., the highest probability, as the body part of interest. For example, assume that there is obtained as the evaluation values a result such that the probability that the image is of the mammary gland is 70%, the probability that the image is of the thyroid gland is 10%, the probability that the image is of the carotid artery is 10%, the probability that the image is of the lower-limb veins is 5%, and the probability that the image is of the lower-limb arteries 5%. In this case, the processor 7 identifies the body part of interest to be the mammary gland.

Next, at Step S3, the processor 7 determines parameters regarding acquisition of data for a color Doppler image according to the body part of interest identified at Step S2. The parameters regarding acquisition of data for a color Doppler image include at least one of scan parameters for a color Doppler scan and those used for color Doppler image data creation based on echo data obtained by the color Doppler scan. The parameters include the number of acoustic lines and transmission frequency in the color Doppler scan, the kind of wall filter, and the like. The parameters are, however, not limited thereto.

Determination of the parameters will now be described in detail. The memory 9 stores therein parameters according to each of a plurality of body parts of the patient serving as a candidate for the body part of interest. The phrase "parameters according to each of a plurality of body parts of a patient" refers to parameters with values suitable for acquisition of data for a color Doppler image for each of a plurality of body parts. The phrase "suitable for acquisition of data for a color Doppler image" means that a color Doppler image representing information on fluids including blood flow as correctly as possible can be obtained. The parameters determined by the processor 7 are a subset of the parameters stored in the memory 9, which subset is stored for the body part of interest identified at Step S2.

Figure 4:
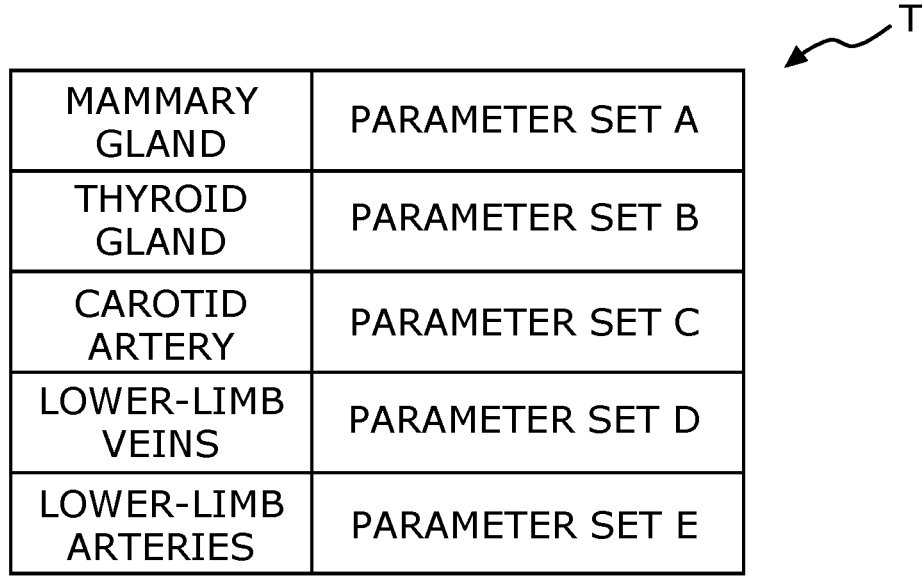
FIG. 4 is a diagram showing an example of a table defining a plurality of body parts of a patient, and a parameter set according to each of the plurality of body parts.

The parameters stored in the memory 9 may be parameter sets each corresponding to each of a plurality of body parts of the patient. For example, as shown in FIG. 4, a table T may be stored in the memory 9, wherein are defined a parameter set A for the mammary gland suitable for acquisition of a color Doppler image of the mammary gland, a parameter set B for the thyroid gland suitable for acquisition of a color Doppler image of the thyroid gland, a parameter set C for the carotid artery suitable for acquisition of a color Doppler image of the carotid artery, a parameter set D for the lower-limb veins suitable for acquisition of a color Doppler image of the lower-limb veins, and a parameter set E for the lower-limb arteries that is suitable for acquisition of a color Doppler image of the lower-limb arteries. Each of the parameter sets A to E includes a plurality of parameters.

The processor 7 determines one of the parameter sets A to E that is stored for the body part of interest identified at Step S2. In the case that the body part of interest identified at Step S2 is the mammary gland, the parameter set A is determined.

Next, at Step S4, data for a color Doppler image is acquired. Specifically, the processor 7 controls the ultrasonic probe 2 to perform a color Doppler scan for a color Doppler image on the patient. The processor 7 also creates data for a color Doppler image based on echo data obtained by the color Doppler scan. In the color Doppler scan and color Doppler image data creation, parameters determined at Step S3 are employed.

Figure 5:
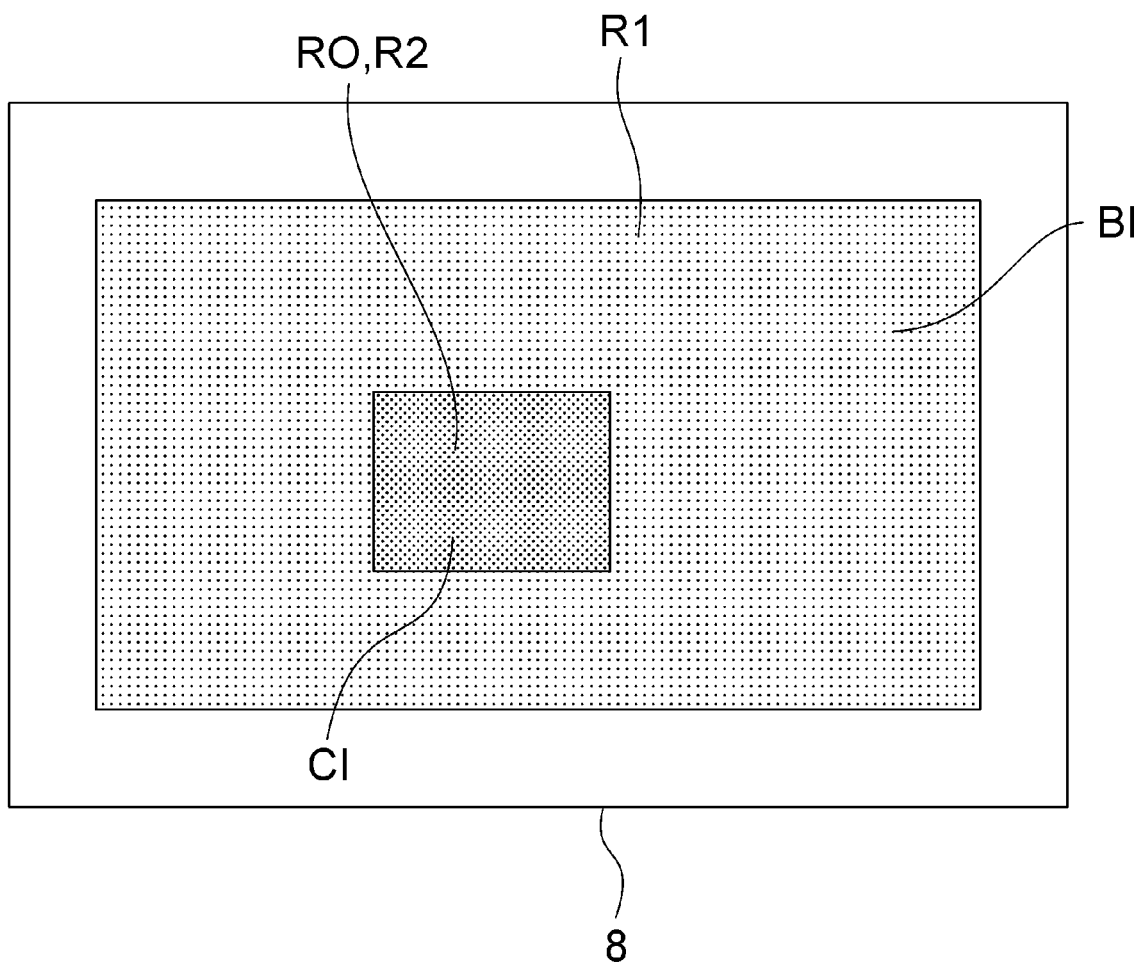
FIG. 5 is a diagram showing the display on which a color Doppler image is displayed.

Moreover, at Step S4, the processor 7 displays on the display 8 a color Doppler image CI based on the data for the color Doppler image, as shown in FIG. 5. The color Doppler image CI is displayed in an overlaid manner onto the B-mode image BI in the region of interest RO.

According to the present embodiment, the operator only needs to perform a B-mode scan using the ultrasonic probe, whereupon a body part of interest serving as a target for producing a color Doppler image is identified, and parameters regarding acquisition of data for a color Doppler image are determined according to the body part of interest. In acquiring a color Doppler image, a B-mode image is acquired before the color Doppler image in most cases, and therefore, parameters regarding acquisition of data for a color Doppler image can be appropriately set according to the body part of interest without imposing any additional workflow or input on the operator.

The processing at Steps S1 to S4 need not be performed for every frame. This implies that the parameters regarding acquisition of data for a color Doppler image need not be determined for every frame. For example, parameters regarding acquisition of data for a color Doppler image may be determined at intervals of a specific period of time longer than a frame-to-frame time interval by performing the processing at Steps S1 to S4 at intervals of the specific period of time. Moreover, the processing at Steps S1 to S4 may be performed at the time of unfreezing, or after recording the data for the B-mode image and the data for the color Doppler image. Furthermore, the processing at Steps S1 to S4 may be performed in the case that the sum of all pixels in one frame of the B-mode image data is different from frame to frame by an amount exceeding a specific threshold.

Figure 6:
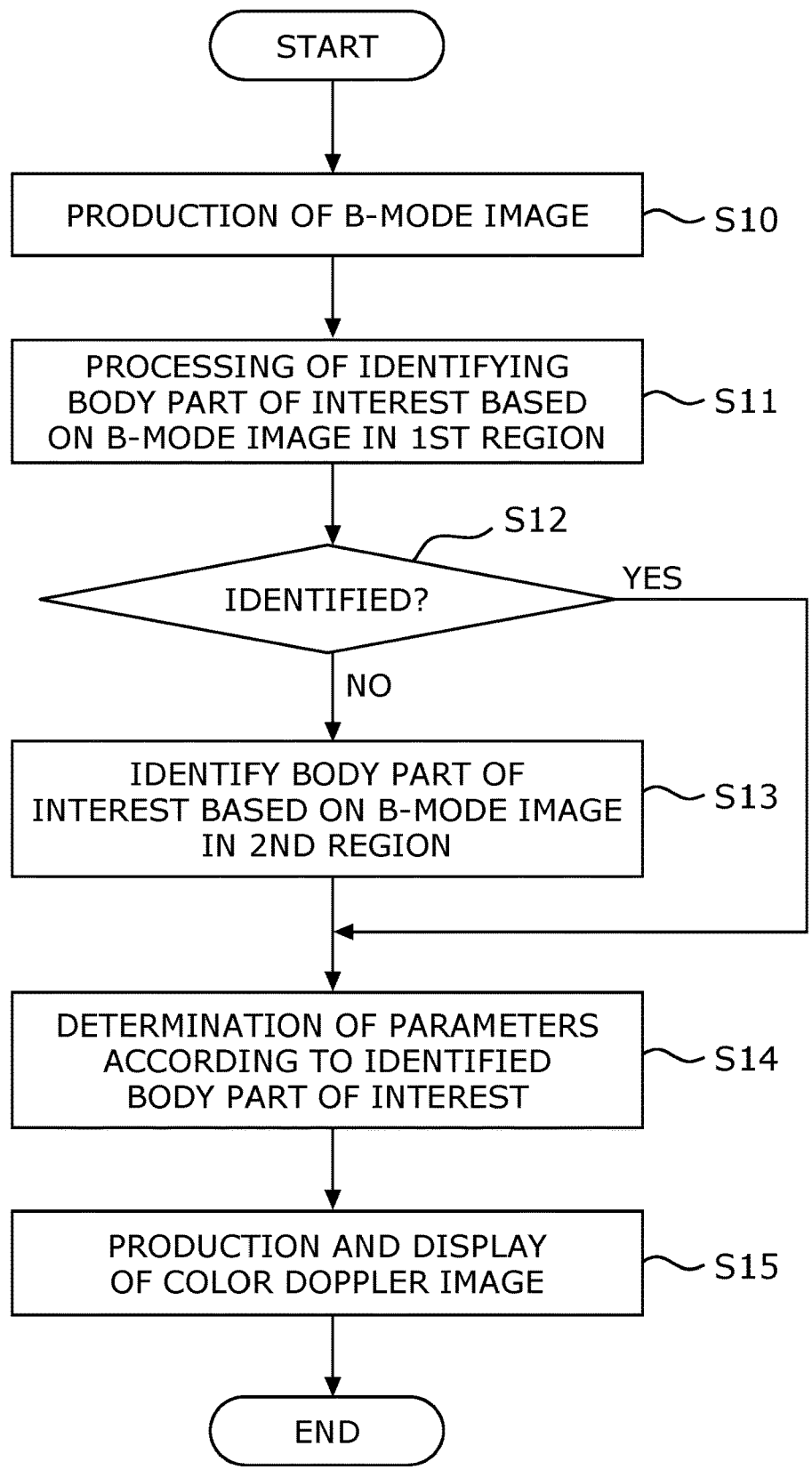
FIG. 6 is a flow chart showing an example of processing in the ultrasonic image display system in accordance with a first variation of the first embodiment.

Next, a variation of the first embodiment will be described. To begin with, a first variation will be described. In an ultrasonic image display system 1 of the first variation, processing following the flow chart in FIG. 6 is performed. At Step S10, processing similar to that at Step S1 is performed, and a B-mode image BI is produced and displayed. In the B-mode image BI, a region of interest RO is defined.

At Step S11, the processor 7 performs processing of identifying a body part of interest serving as a target for producing a color Doppler image based on the data for the B-mode image BI in a first region greater than the region of interest RO. The first region includes the whole or part of the acquired B-mode image BI. The processing of identifying a body part of interest is processing of obtaining an evaluation value using the learned model described earlier, in an example.

At Step S12, the processor 7 decides whether or not a body part of interest can be identified based on the evaluation value obtained at Step S11. For example, in the case that the evaluation value is the probability described earlier, the processor 7 decides whether or not the body part of interest can be identified based on a difference D between the highest evaluation value and second highest evaluation value. In the case that the difference D exceeds a threshold, the processor 7 decides that the body part of interest can be identified, and identifies a body part with the highest evaluation value as the body part of interest ("Yes" at Step S12). Upon identifying the body part of interest, the processing goes to Step S14. On the other hand, in the case that the difference D is equal to or less than the threshold, the processor 7 decides that the body part of interest cannot be identified ("No" at Step S12). In the case that the body part of interest is not identified, the processing goes to Step S13.

At Step S13, the processor 7 performs processing of identifying a body part of interest serving as a target for producing a color Doppler image based on the data for the B-mode image BI in the second region R2, i.e., in the region of interest RO. The processing, again, is processing of obtaining an evaluation value using the learned model described earlier, in an example. The processor 7 identifies a body part with the highest evaluation value as the body part of interest.

Processing at Steps S14 and S15 is processing similar to that at Steps S3 and S4.

Figure 7:
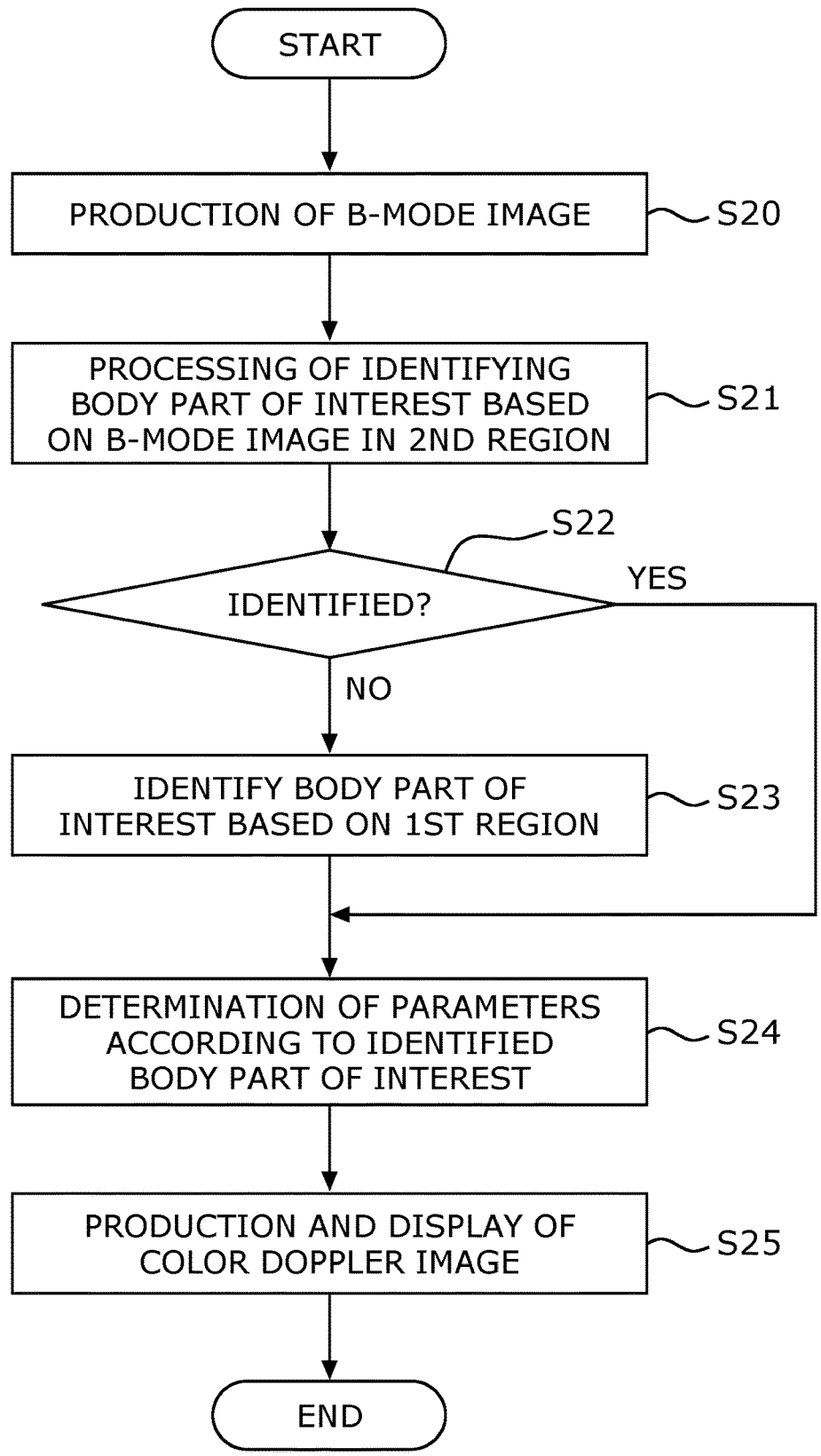
FIG. 7 is a flow chart showing an example of processing in the ultrasonic image display system in accordance with a first variation of the first embodiment.

Next, a second variation will be described. In an ultrasonic image display system 1 of the second variation, processing following the flow chart in FIG. 7 is performed. In the flow chart in FIG. 7, processing at Steps S20, S22, S24, and S25 is the same as that at Steps S10, S12, S14, and S15. At Step S21, similarly to Step S13, the processor 7 performs the processing of identifying a body part of interest serving as a target for producing a color Doppler image based on the data for the B-mode image BI in the second region R2, i.e., in the region of interest RO.

At Step S23, similarly to Step S11, the processor 7 performs processing of identifying a body part of interest serving as a target for producing a color Doppler image based on the data for the B-mode image BI in the first region. The processor 7 also identifies a body part with the highest evaluation value obtained using the learned model described earlier, as the body part of interest.

Again, determination of the parameters regarding acquisition of data for a color Doppler image need not be performed for every frame in the first and second variations.

Next, a second embodiment will be described. An ultrasonic image display system in the second embodiment is the ultrasonic image display system 1 having the configuration shown in FIG. 1. A description of the configuration will be omitted. Now processing in the ultrasonic image display system 1 of the present embodiment will be described hereinbelow.

Figure 8:
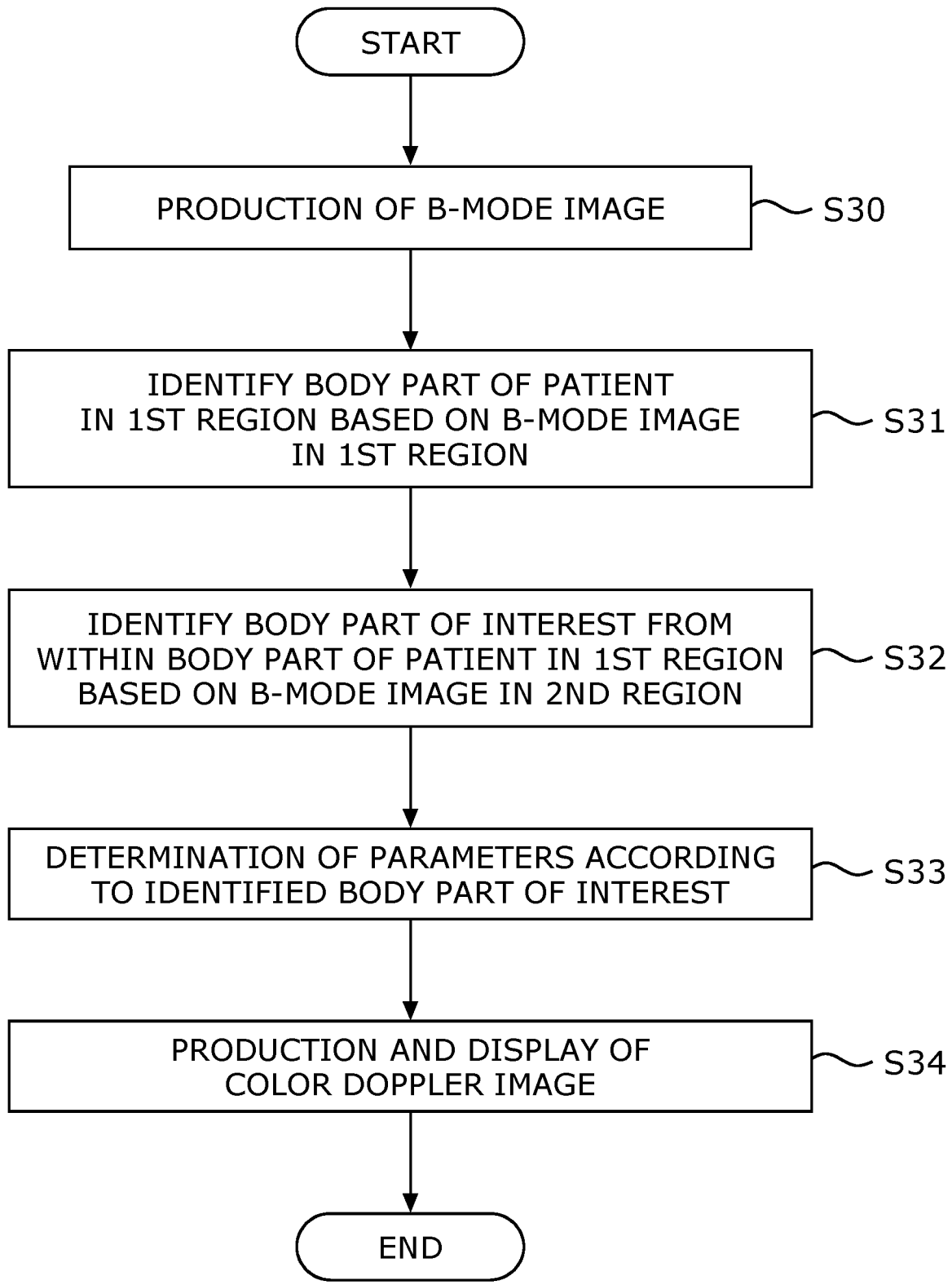
FIG. 8 is a flow chart showing an example of processing in the ultrasonic image display system in accordance with a second embodiment.

In the flow chart in FIG. 8, processing similar to that at Steps S1, S10 and S20 in the first embodiment is performed at Step S30, and a B-mode image BI is produced and displayed. In the B-mode image BI, a region of interest RO is defined.

Next, at Step S31, the processor 7 identifies a body part of the patient in a first region greater than the region of interest RO based on the data for the B-mode image BI in the first region. The first region is the whole or part of the acquired B-mode image BI, as in the first embodiment. The first region includes the region of interest RO. The first region here is assumed to be the first region R1 that is the whole of the B-mode image BI shown in FIG. 3.

The processor 7 may perform identification of the body part using a learned model obtained by machine learning. This will now be particularly described. The memory 9 stores therein a first learned model trained for a correlation between a B-mode image and a first evaluation value for the B-mode image. The first evaluation value is related to a body part of the patient. In an example, the first evaluation value is the probability that the B-mode image matches an image of a body part of the patient. In the first learned model, a first evaluation value is learned for each of a plurality of body parts of the patient. In an example, the body part of the patient is the mammary gland, neck, and lower limbs, and the first learned model has correlations learned between a B-mode image and each of the probabilities that the B-mode image is of the mammary gland, that it is of the neck, and that it is of the lower limbs. The body part of the patient may also be the mammary gland, thyroid gland, carotid artery, lower-limb veins, and lower-limb arteries, and the first learned model may have correlations learned between a B-mode image and each of the probabilities that the B-mode image is of the mammary gland, that it is of the thyroid gland, that it is of the carotid artery, that it is of the lower-limb veins, and that it is of the lower-limb arteries. The body part of the patient is, however, not limited thereto.

The processor 7 inputs the data for the B-mode image BI in the first region R1 acquired at Step S30 to an input layer of the learned model. The processor 7 then obtains a first evaluation value for a body part of the patient in the first region R1 as an output of an output layer of the first learned model. In an example, the first evaluation value is the probability that the B-mode image BI in the first region R1 of the data input to the first learned model matches an image of each of the body parts of the patient.

In the case that the first learned model has probabilities learned for an image of the mammary gland, an image of the neck, and an image of the lower limbs, the first evaluation values are the probabilities that the B-mode image BI in the first region R1 is of the mammary gland, that it is of the neck, and that it is of the lower limbs. In the case that the first learned model has probabilities learned for an image of the mammary gland, an image of the thyroid gland, an image of the carotid artery, an image of the lower-limb veins, and an image of the lower-limb arteries, the first evaluation values are the probabilities that the B-mode image BI in the first region R1 is of the mammary gland, that it is of the thyroid gland, that it is of the carotid artery, that it is of the lower-limb veins, and that it is of the lower-limb arteries.

The processor 7 identifies the body part of the patient in the first region R1 based on the first evaluation value. In an example, the processor 7 identifies a body part with the highest first evaluation value i.e., the highest probability. For example, in the case that there are obtained the first evaluation values such that the probability of an image of the mammary gland is 10%, the probability of an image of the neck is 80%, and the probability of an image of the lower limbs is 10%, the processor 7 identifies the body part of the patient in the first region R1 to be the neck.

In another example, in the case that a difference D between the highest first evaluation value and second highest first evaluation value is equal to or less than a threshold, the processor 7 identifies a body part with the highest first evaluation value and a body part with the second highest first evaluation value as the body parts of the patient in the first region R1. For example, assume that there is obtained a result such that the probability of an image of the mammary gland is 10%, the probability of an image of the thyroid gland is 38%, the probability of an image of the carotid artery is 42%, the probability of an image of the lower-limb veins is 5%, and the probability of an image of the lower-limb arteries is 5%. For example, in the case that the threshold for the difference D is 5%, the processor 7 identifies the body part of the patient in the first region R1 to be the thyroid gland and carotid artery. The processor 7 may identify the neck in which the thyroid gland and carotid artery are included as the body part of the patient in the first region R1.

Next, at Step S32, the processor 7 identifies a body part of interest serving as a target for producing a color Doppler image based on the data for the B-mode image in the second region R2. The second region R2 is the region of interest RO. The body part of interest is included in the body part of the patient in the first region R1 identified at Step S31. Therefore, the processor 7 identifies the body part of interest from within the body part of the patient in the first region R1 identified at Step S31. For example, in the case that the body part of the patient in the first region is identified to be the thyroid gland and carotid artery, or to be the neck, the thyroid gland or carotid artery included in the neck are identified as the body part of interest.

The processor 7 may perform identification of the body part of interest using a learned model obtained by machine learning. This will now be particularly described. The memory 9 stores therein a second learned model trained for a correlation between a B-mode image and a second evaluation value for the B-mode image. The second evaluation value is related to a body part included in a body part of the patient and serving as a candidate for the body part of interest. In an example, the second evaluation value is the probability that the B-mode image matches an image of a body part serving as a candidate for the body part of interest. The second learned model is stored for each of a plurality of body parts of the patient. The expression "body part of the patient" as used herein refers to a body part that includes a body part serving as a candidate for the body part of interest and is in a region greater than the body part serving as the candidate for the body part of interest. For example, in the case that the body part serving as a candidate for the body part of interest is the thyroid gland, carotid artery, lower-limb veins, and lower-limb arteries, a second learned model for the neck and that for the lower limbs are stored in the memory 9. Here, the second learned model for the neck is designated as a second learned model SLM1, and that for the lower limbs as a second learned model SLM2. The second learned model SLM1 for the neck may be a learned model for a region including the thyroid gland and carotid artery. Similarly, the second learned model SLM2 for the lower limbs may be a learned model for a region including the lower-limb veins and lower-limb arteries.

The second learned model SLM1 for the neck is trained for a correlation between a B-mode image and each of the probabilities that the B-mode image is of the thyroid gland and that it is of the carotid artery. The second learned model SLM2 for the lower limbs is trained for a correlation between a B-mode image and each of the probabilities that the B-mode image is of the lower-limb veins and that it is of the lower-limb arteries.

The processor 7 identifies the body part of interest using one of the second learned models SLM1 and SLM2 that is regarding the body part identified at Step S31. In the case that the body part identified at Step S31 is the thyroid gland and carotid artery, or the neck, the second learned model SLM1 is used to identify the body part of interest. Specifically, the data for the B-mode image in the second region R2 is input to an input layer of the second learned model SLM1. The processor 7 then obtains a second evaluation value related to the body part of the patient in the second region R2 as an output of an output layer of the second learned model SLM1.

In an example, the second evaluation value is the probability that the B-mode image BI in the second region R2 matches an image of each of the body parts serving as a candidate for the body part of interest. Since the second learned model SLM1 is the learned model for the neck, the second evaluation values are the probabilities that the B-mode image BI in the second region R2 is of the thyroid gland and that it is of the carotid artery.

For the lower limbs, the second evaluation values output from an output layer of the second learned model SLM2 are the probabilities that the B-mode image BI in the second region R2 is of the lower-limb veins and that it is of the lower-limb arteries.

The processor 7 identifies the body part of interest based on the second evaluation value. In an example, the processor 7 identifies a body part with the highest second evaluation value. For example, in the case that there are obtained the second evaluation values such that the probability of an image of the thyroid gland is 80% and the probability of an image of the carotid artery is 20%, the processor 7 identifies the body part of interest to be the thyroid gland.

Processing at Steps S33 and S34 after the body part of interest has been identified at Step S32 is similar to that at Steps S3 and S4, Steps S14 and S15, and Steps S24 and S25.

According to the present embodiment, as in the first embodiment, parameters regarding acquisition of data for a color Doppler image can be appropriately set according to the body part of interest without imposing any additional workflow or input on the operator. Moreover, according to the present embodiment, after the body part of the patient including the body part of interest has been first identified at Step S31, the body part of interest is identified from within the body part, and therefore, the body part of interest can be more correctly identified.

The processing at Steps S30 to S34 need not be performed for every frame, as in the first embodiment.

Figure 9:
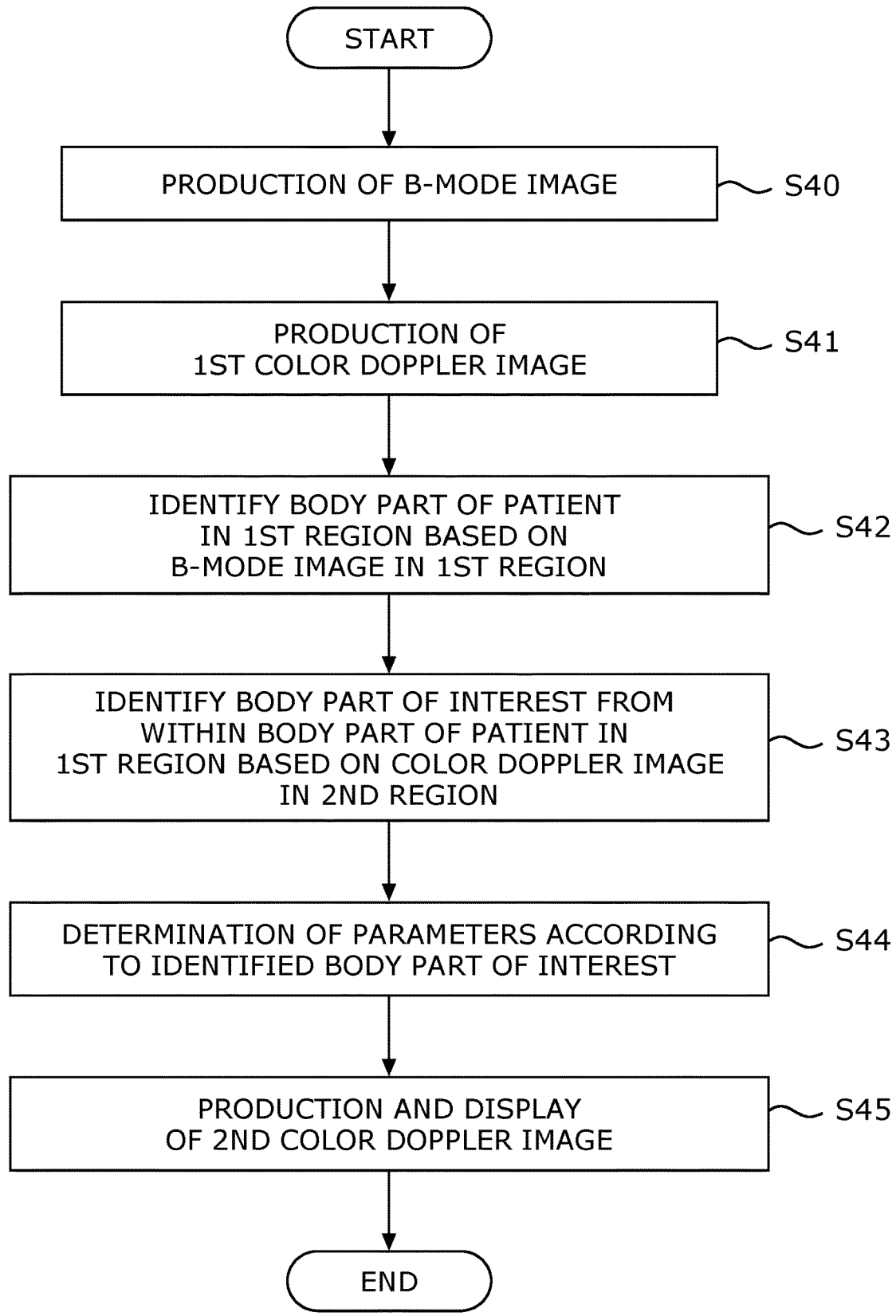
FIG. 9 is a flow chart showing an example of processing in the ultrasonic image display system in accordance with a variation of the second embodiment.

Next, a variation of the second embodiment will be described. In this variation, processing following the flow chart in FIG. 9 is performed. First, at Step S40, processing similar to that at Steps S1, S10, S20, and S30 is performed, and a B-mode image BI is produced and displayed. In the B-mode image BI, a region of interest RO is defined.

Next, at Step S41, the processor 7 controls the ultrasonic probe 2 to perform a first color Doppler scan for a first color Doppler image on the patient. The processor 7 also creates data for a first color Doppler image in a region of interest RO based on echo data obtained by the first color Doppler scan.

Parameters used in the first color Doppler scan and first color Doppler image data creation are suboptimal parameters according to the body part providing at least minimal blood flow information for any body part. The parameters used in the first color Doppler scan and first color Doppler image data creation are different from those used in a second color Doppler scan and second color Doppler image data creation, which will be discussed later, the latter being optimal parameters according to the body part.

Figure 10:
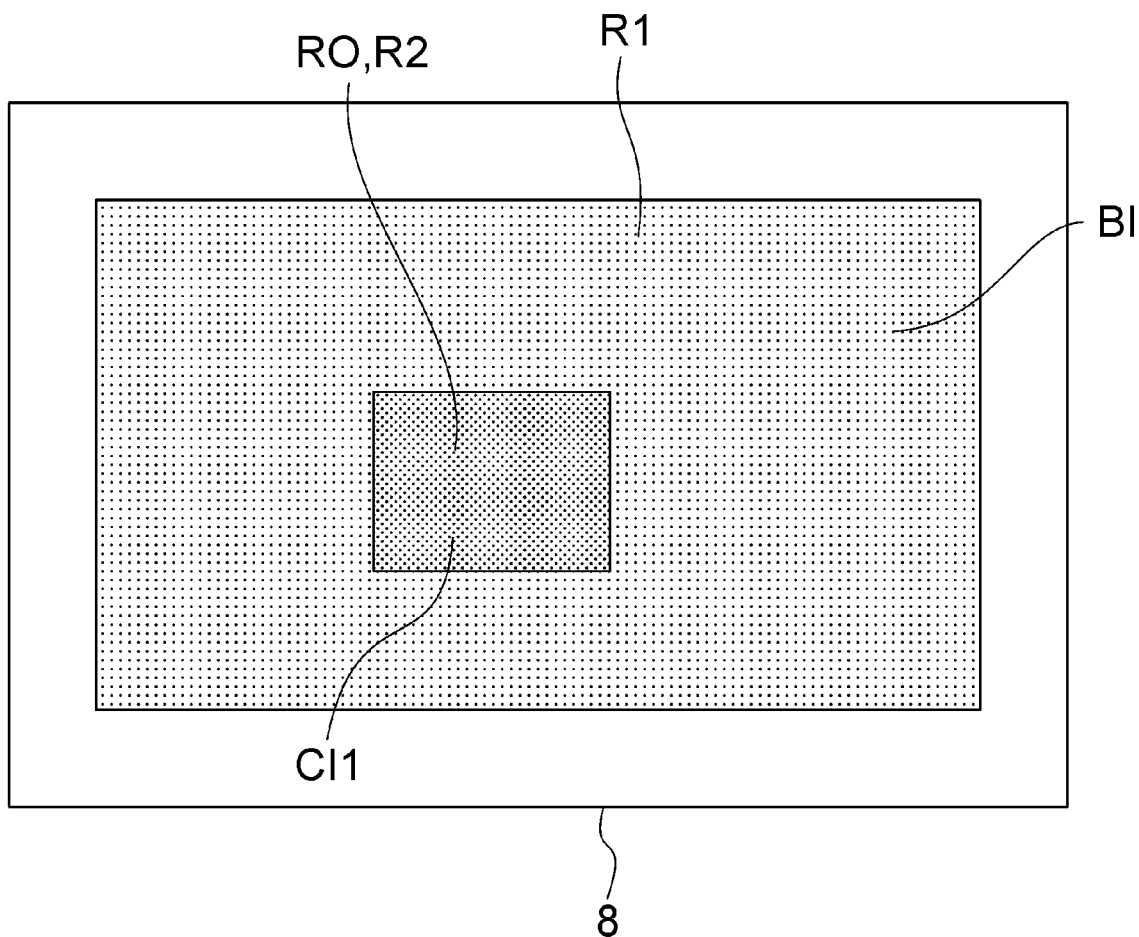
FIG. 10 is a diagram showing the display on which a first color Doppler image is displayed in the variation of the second embodiment.

At Step S41, the processor 7 displays a first color Doppler image CI1 on the display 8 based on the data for the first color Doppler image, as shown in FIG. 10. The first color Doppler image CI1 is displayed in an overlaid manner onto the B-mode image BI in the region of interest RO.

Next, at Step S42, processing similar to that at Step S31 is performed, and a body part of the patient in the first region R1 is identified.

Next, at Step S43, the processor 7 identifies a body part of interest serving as a target in the region of interest RO in the patient based on the data for the first color Doppler image CI1 in the second region R2, i.e., in the region of interest RO. The body part of interest is a body part of the patient that was the target for producing the first color Doppler image CI1, and at the same time, it is a body part of the patient that is to be a target for producing a second color Doppler image CI2, which will be discussed later. Similarly to the description regarding Step S32, the body part of interest is included in the body part of the patient in the first region R1 identified at Step S42.

The processor 7 may perform identification of the body part of interest using a learned model obtained by machine learning. This will now be particularly described. The memory 9 stores therein a second learned model trained for a correlation between a color Doppler image and a second evaluation value for the color Doppler image. The second evaluation value, again, is related to a body part included in a body part of the patient and serving as a candidate for the body part of interest. In an example, the second evaluation value is the probability that the color Doppler image matches an image of a body part serving as a candidate for the body part of interest. The second learned model is stored for each of a plurality of body parts of the patient, as in the embodiment described earlier. Here, again, a second learned model for the neck is designated as a second learned model SLM1, and that for the lower limbs as a second learned model SLM2.

In this variation, however, the second learned model for the neck SLM1 is trained for a correlation between a color Doppler image and each of the probabilities that the color Doppler image is of the thyroid gland and that it is of the carotid artery. Moreover, the second learned model SLM2 for the lower limbs is trained for a correlation between a color Doppler image and each of the probabilities that the color Doppler image is of the lower-limb veins and that it is of the lower-limb arteries.

The processor 7 identifies the body part of interest using one of the second learned models SLM1 and SLM2 that is regarding the body part identified at Step S42. In the case that the body part identified at Step S42 is the thyroid gland and carotid artery, or the neck, the second learned model SLM1 is used to identify the body part of interest. Specifically, the data for the first color Doppler image CD in the second region R2 is input to an input layer of the second learned model SLM1. The processor 7 then obtains a second evaluation value related to the body part of the patient in the second region R2 as an output of an output layer of the second learned model SLM1.

In an example, the second evaluation value is the probability that the first color Doppler image CD in the second region R2 matches an image of each of the body parts serving as a candidate for the body part of interest. Since the second learned model SLM1 is the learned model for the neck, the second evaluation values are the probabilities that the first color Doppler image CI1 in the second region R2 is of the thyroid gland and that it is an image of the carotid artery.

For the lower limbs, the second evaluation values output from an output layer of the second learned model SLM2 are the probabilities that the first color Doppler image CI1 in the second region R2 is of the lower-limb veins and that it is of the lower-limb arteries.

The processor 7 identifies the body part of interest based on the second evaluation value, as in Step S32.

Processing at Steps S44 and S45 after the body part of interest has been identified at Step S43 is basically similar to that at Steps S3 and S4, Steps S14 and S15, Steps S24 and S25, and Steps S33 and S34. However, at Step S44, parameters regarding acquisition of data for a second color Doppler image are determined. The parameters determined here are those according to the body part of interest, and are different from those regarding acquisition of data for the first color Doppler image.

Figure 11:
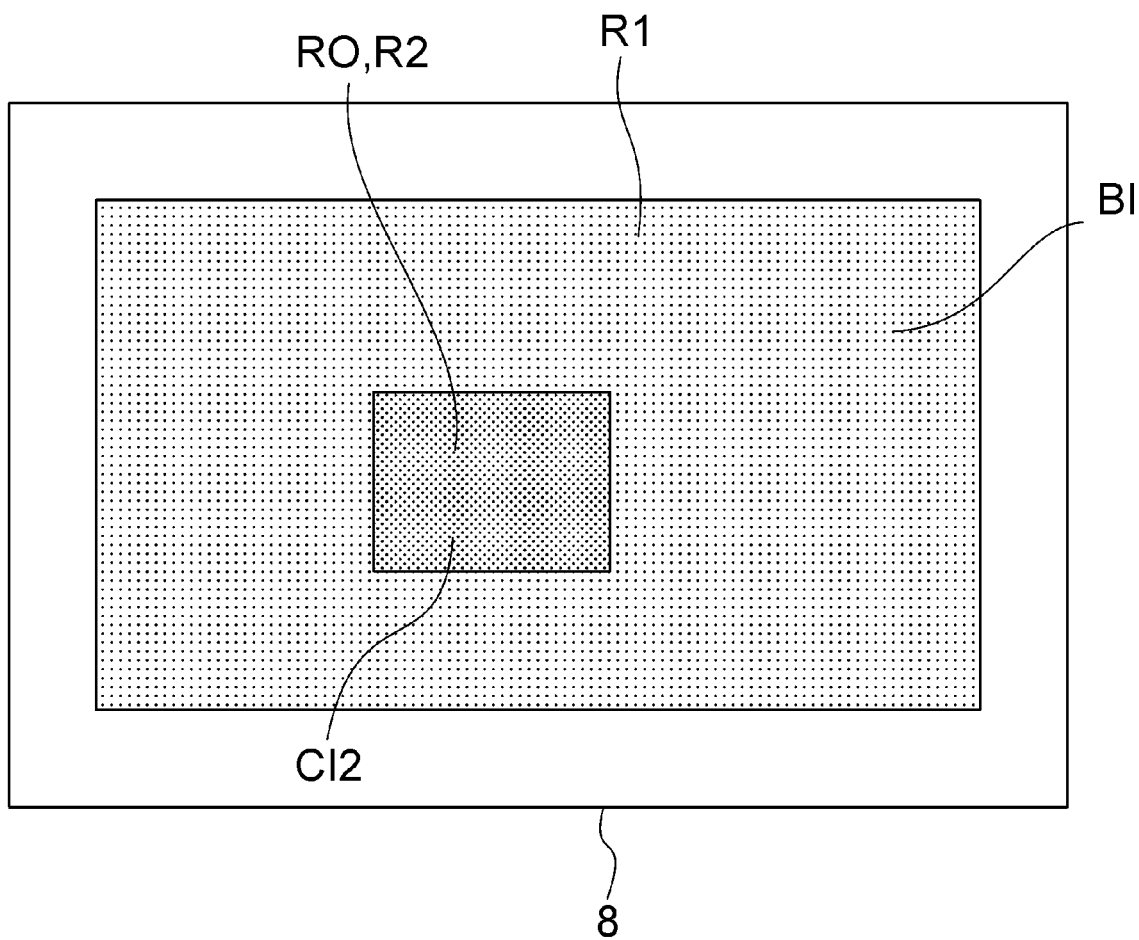
FIG. 11 is a diagram showing the display on which a second color Doppler image is displayed in the variation of the second embodiment.

Moreover, at Step S45, the parameters determined at Step S44 are used to perform a second color Doppler scan, and data for a second color Doppler image is created. As shown in FIG. 11, a second color Doppler image CI2 is displayed in an overlaid manner onto the B-mode image in the region of interest RO on the display 8.

While the present invention has been described with reference to particular embodiments, various changes may be made and/or equivalents may be substituted without departing from the scope and spirit of the present invention. In addition, many modifications may be made to adapt a particular situation or material to the teachings of the invention, without departing from the scope and spirit of the present invention. Therefore, the present invention is not limited to the particular embodiments disclosed herein, and it is intended that the present invention will encompass all the embodiments falling within the appended claims.

For example, identification of the body part of interest and identification of the body part of the patient based on the data for the B-mode image described hereinabove is not limited to machine learning-based identification. For example, brightness distribution analysis, such as that for a texture pattern, frequency analysis, and the like, on the data for the B-mode image may be employed. A combination of the foregoing and machine learning may apply as well.

Moreover, the processor 7 may identify the body part of interest serving as a target for producing a color Doppler image based on a position of the second region R2. The position includes a position in the depth of the patient. The processor 7 may identify the body part of interest serving as a target for producing a color Doppler image based on both the data for the B-mode image in the second region and the position of the second region.

Furthermore, the parameters determined according to the body part of interest may be applied to only one of the color Doppler scan and color Doppler image data creation.

The embodiments described above may be a method of controlling an ultrasonic image display system comprising a processor and an ultrasonic probe, said method of controlling comprising using said processor to:
  control said ultrasonic probe to perform a B-mode scan for a B-mode image on a patient;
  create data for a B-mode image based on echo data obtained by said B-mode scan;
  identify a body part of interest serving as a target for producing a color Doppler image of said patient based on the data for said B-mode image;
  determine parameters regarding acquisition of data for said color Doppler image according to said body part of interest;
  control said ultrasonic probe to perform a color Doppler scan for a color Doppler image on said patient; and
  create data for a color Doppler image based on echo data obtained by said color Doppler scan, wherein
  at least one of said color Doppler scan and said color Doppler image data creation is performed using said parameters.

The embodiments described above may also be a method of controlling an ultrasonic image display system comprising a processor and an ultrasonic probe, said method of controlling comprising using said processor to:
  control said ultrasonic probe to perform a B-mode scan for a B-mode image on a patient;
  create data for a B-mode image based on echo data obtained by said B-mode scan;
  define a region of interest in said B-mode image;
  control said ultrasonic probe to perform a first color Doppler scan for a first color Doppler image on said patient;
  create data for a first color Doppler image in said region of interest based on echo data obtained by said first color Doppler scan;
  identify a body part of said patient in a first region in said patient based on the data for said B-mode image in said first region, said first region including said region of interest;
  identify a body part of interest serving as a target in said region of interest in said patient based on the data for said first color Doppler image in a second region constituted by said region of interest, said body part of interest being included in the body part of said patient in said first region;

determine parameters regarding acquisition of data for a second color Doppler image of said patient according to said body part of interest;

control said ultrasonic probe to further perform a second color Doppler scan for said second color Doppler image on said patient; and create data for said second color Doppler image based on echo data obtained by said second color Doppler scan, wherein at least one of said color Doppler scan and said second color Doppler image data creation is performed using said parameters.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. An ultrasonic image display system comprising:
a display;
a memory storing therein a first learned model trained for a correlation between a B-mode image and an evaluation value for said B-mode image, and a second learned model trained for a correlation between a color Doppler image and a second evaluation value for said color Doppler image;
an ultrasonic probe having a transmitter and a receiver; and
a processor being adapted to perform control comprising the acts of:
controlling said ultrasonic probe to perform a B-mode scan for a B-mode image on a patient;
creating data for a B-mode image based on echo data obtained by said B-mode scan;
defining a region of interest in said B-mode image;
controlling said ultrasonic probe to perform a first color Doppler scan for a first color Doppler image on said patient;
creating data for said first color Doppler image in said region of interest based on echo data obtained by said first color Doppler scan;
displaying the first color Doppler image on the display;
identifying a body part of said patient in a first region in said patient by inputting the data for said B-mode image in said first region into the first learned model, said first region including said region of interest;
identifying a body part of interest serving as a target in said region of interest in said patient by inputting the data for said first color Doppler image in a second region constituted by said region of interest into the second learned model, said body part of interest being included in the body part of said patient in said first region;

determining parameters regarding acquisition of data for a second color Doppler image of said patient according to said body part of interest;

generating control signals for controlling one or more of the transmitter and the receiver of said ultrasonic probe to further perform a second color Doppler scan on said patient based on the determined parameters;

creating data for said second color Doppler image based on echo data obtained by said second color Doppler scan; and displaying said second color Doppler image on the display.

2. The ultrasonic image display system as recited in claim 1, wherein: said processor performs the processing of identifying said body part of interest based on a position of said second region.

3. The ultrasonic image display system as recited in claim 1, comprising:
memory for storing therein said parameters according to each of a plurality of body parts of the patient serving as a candidate of said body part of interest, and
the parameters determined by said processor are those of the parameters stored in said memory that are stored for said body part of interest identified by said processor.

4. The ultrasonic image display system as recited in claim 3, wherein:
the parameters stored in said memory constitute a parameter set according to each of the plurality of body parts of said patient, each of said parameter sets comprising a plurality of parameter values, and
the parameters determined by said processor constitute one of the parameter sets stored in said memory that is stored for said body part of interest identified by said processor.

5. An ultrasonic image display system comprising a display, a processor, memory, and an ultrasonic probe, said processor being adapted to perform control comprising the acts of:
controlling said ultrasonic probe to perform a B-mode scan for a B-mode image on a patient;
creating data for a B-mode image based on echo data obtained by said B-mode scan;
defining a region of interest in said B-mode image;
controlling said ultrasonic probe to perform a first color Doppler scan for a first color Doppler image on said patient;
creating data for said first color Doppler image in said region of interest based on echo data obtained by said first color Doppler scan;
displaying the first color Doppler image on the display;
identifying a body part of said patient in a first region in said patient based on the data for said B-mode image in said first region, said first region including said region of interest;
identifying a body part of interest serving as a target in said region of interest in said patient based on the data for said first color Doppler image in a second region constituted by said region of interest, said body part of interest being included in the body part of said patient in said first region;
determining parameters regarding acquisition of data for a second color Doppler image of said patient according to said body part of interest;

generating control signals for controlling one or more of the transmitter and the receiver of said ultrasonic probe to further perform a second color Doppler scan on said patient based on the determined parameters;

creating data for said second color Doppler image based on echo data obtained by said second color Doppler scan; and displaying said second color Doppler image on the display;

wherein said memory is configured for storing a first learned model trained for a correlation between a B-mode image and a first evaluation value for said B-mode image, and a second learned model trained for a correlation between a color Doppler image and a second evaluation value for said color Doppler image, said first evaluation value being related to a body part of the patient, said second evaluation value being related to a body part included in the body part of the patient and serving as a candidate for said body part of interest, said second learned model being stored for each of a plurality of body parts of the patient, the processing of identifying said body part based on data for the B-mode image in said first region comprises processing of: inputting the data for said B-mode image in said first region to an input layer of said first learned model; obtaining, as an output of an output layer of said first learned model, said first evaluation value for the B-mode image of said data input to said input layer; and identifying said body part based on said first evaluation value, and the processing of identifying said body part of interest based on the data for said first color Doppler image in said second region comprises processing of: inputting the data for said first color Doppler image to an input layer of said second learned model that is regarding said body part identified based on the B-mode image in said first region; obtaining, as an output of an output layer of said second learned model, said second evaluation value for the first color Doppler image of said data input to said input layer; and identifying said body part of interest based on said second evaluation value.

6. The ultrasonic image display system as recited in claim 5, wherein:

said first evaluation value is a probability that said B-mode image matches an image of a body part of said patient, and said second evaluation value is a probability that said color Doppler image and said first color Doppler image match an image of the body part included in the body part of said patient and serving as a candidate for said body part of interest.

7. An ultrasonic image display system comprising:

a display;

a memory storing therein a first learned model trained for a correlation between a B-mode image and an evaluation value for said B-mode image, and a second learned model trained for a correlation between a color Doppler image and a second evaluation value for said color Doppler image, said first evaluation value being related to a body part of the patient, said second evaluation value being related to a body part included in the body part of the patient and serving as a candidate for said body part of interest, said second learned model being stored for each of a plurality of body parts of the patient;

an ultrasonic probe having a transmitter and a receiver; and a processor being adapted to perform control comprising the acts of:

controlling said ultrasonic probe to perform a B-mode scan for a B-mode image on a patient;

creating data for a B-mode image based on echo data obtained by said B-mode scan;

controlling said ultrasonic probe to perform a first color Doppler scan for a first color Doppler image on said patient;

creating data for said first color Doppler image in based on echo data obtained by said first color Doppler scan;

displaying the first color Doppler image on the display;

identifying a body part of interest by inputting the data for said B-mode image in said first region into the first learned model and by inputting the data for said first color Doppler image in a second region constituted by said region of interest into the second learned model;

determining parameters regarding acquisition of data for a second color Doppler image of said patient according to said body part of interest;

generating control signals for controlling one or more of the transmitter and the receiver of said ultrasonic probe to further perform a second color Doppler scan on said patient based on the determined parameters;

creating data for said second color Doppler image based on echo data obtained by said second color Doppler scan; and displaying said second color Doppler image on the display.

* * * * *